US00PP33627P2

(12) United States Plant Patent
Flore

(10) Patent No.: US PP33,627 P2
(45) Date of Patent: Nov. 9, 2021

(54) ***PHALAENOPSIS* PLANT NAMED 'MI01181'**

(50) Latin Name: *Phalaenopsis hybrida*
Varietal Denomination: MI01181

(71) Applicant: Febe Flore, Lochristi (BE)

(72) Inventor: Febe Flore, Lochristi (BE)

(73) Assignee: MICROFLOR N.V., Lochristi (BE)

( * ) Notice: Subject to any disclaimer, the term of this patent is extended or adjusted under 35 U.S.C. 154(b) by 0 days.

(21) Appl. No.: 17/163,515

(22) Filed: Jan. 31, 2021

(51) Int. Cl.
*A01H 5/02* (2018.01)
*A01H 6/62* (2018.01)

(52) U.S. Cl.
USPC ..... Plt./311

CPC ..... *A01H 6/62* (2018.05); *A01H 5/02* (2013.01)

(58) Field of Classification Search
USPC ..... Plt./311
See application file for complete search history.

*Primary Examiner* — Susan McCormick Ewoldt
(74) *Attorney, Agent, or Firm* — C. Anne Whealy

(57) ABSTRACT

A new and distinct cultivar of *Phalaenopsis* plant named 'MI01181', characterized by its upright plant habit; vigorous growth habit; strong flowering stems; strong and relatively small leaves; freely flowering habit with typically two inflorescences per plant, each inflorescence with numerous flowers; small white-colored flowers with large red purple-colored lateral spots on the lateral petals; and good post-production longevity and resistance to bud drop during transport.

2 Drawing Sheets

Figure 1:
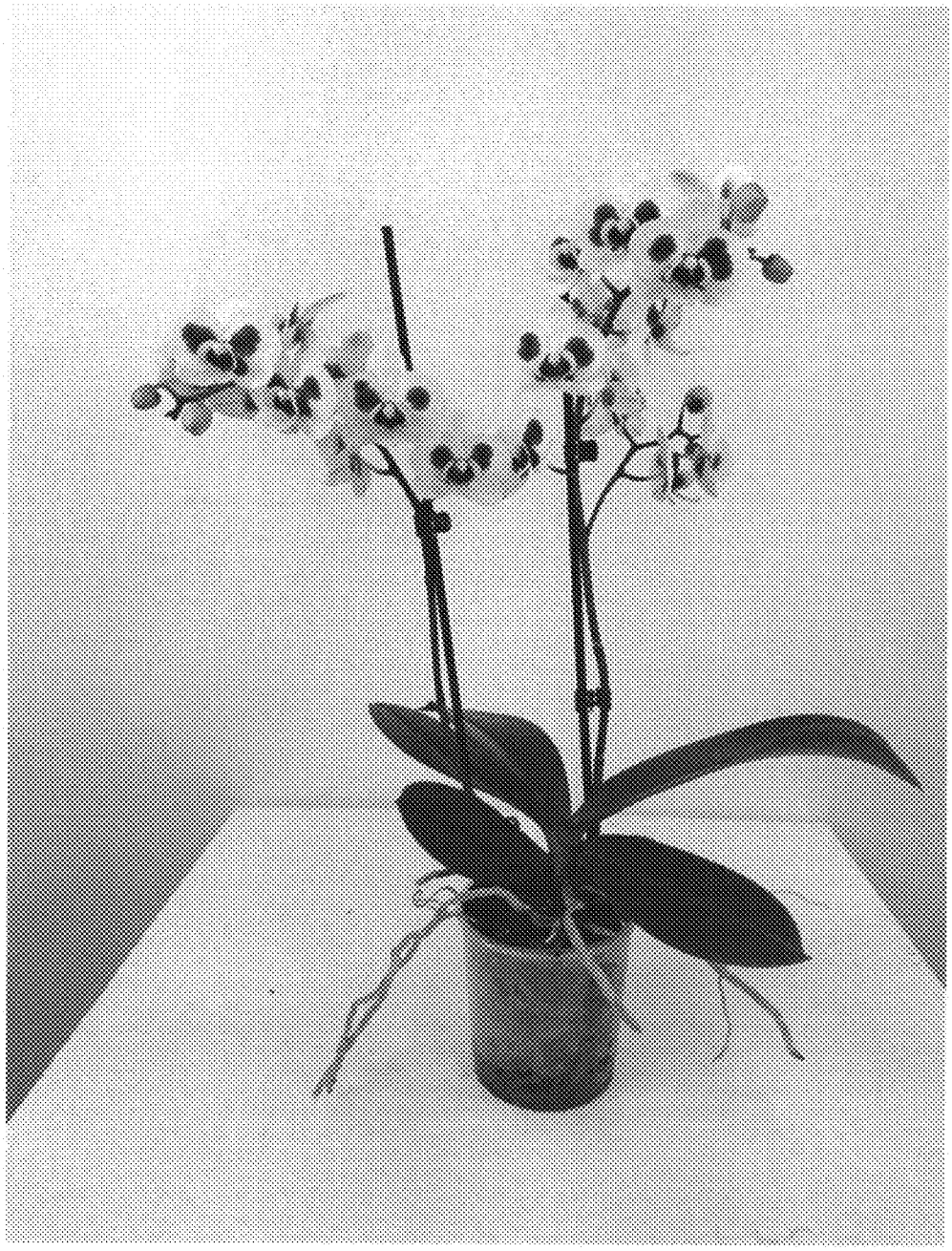

Botanical designation: *Phalaenopsis hybrida.*
Cultivar denomination: 'MI01181'.

STATEMENT REGARDING PRIOR DISCLOSURES BY INVENTOR/APPLICANT

An European Community Plant Breeder's Rights application for the instant plant was filed by the Assignee of the instant application, Microflor N. V. of Lochristi, Belgium on Sep. 21, 2020, application number 2020/2268. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'MI01181'.

The new *Phalaenopsis* plant is a product of a planned breeding program conducted by the Inventor in Lochristi, Belgium. The objective of the breeding program is to develop new freely flowering *Phalaenopsis* plants with good leaf shape and relatively small flowers with unique and attractive flower coloration.

The new *Phalaenopsis* plant originated from a cross-pollination by the Inventor in 2011 in Lochristi, Belgium of a proprietary selection of *Phalaenopsis hybrida* identified as code number PH01616, not patented, as the female, or seed, parent with a proprietary selection of *Phalaenopsis hybrida* identified as code number PH01477, not patented, as the male, or pollen, parent. The new *Phalaenopsis* plant was discovered and selected by the Inventor as a single flowering plant from within the progeny of the stated cross-pollination grown in a controlled greenhouse environment in Lochristi, Belgium in September, 2014.

Asexual reproduction of the new *Phalaenopsis* plant by in vitro meristem propagation in a controlled environment in Lochristi, Belgium since May, 2016 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MI01181'. These characteristics in combination distinguish 'MI01181' as a new and distinct *Phalaenopsis* plant:

1. Upright plant habit.
2. Vigorous growth habit.
3. Strong flowering stems.
4. Strong and relatively small leaves.
5. Freely flowering habit with typically two inflorescences per plant, each inflorescence with numerous flowers.
6. Small white-colored flowers with large red purple-colored lateral spots on the lateral petals.
7. Good postproduction longevity and resistance to bud drop during transport.

Plants of the new *Phalaenopsis* can be compared to plants of the female parent selection. Plants of the new *Phalaenopsis* differ primarily from plants of the female parent selection in the following characteristics:

1. Inflorescences of plants of the new *Phalaenopsis* are shorter than inflorescences of plants of the female parent selection.
2. Plants of the new *Phalaenopsis* have smaller flowers than plants of the female parent selection.
3. The flower labella of plants of the new *Phalaenopsis* are yellow and white in color whereas the flower labella of plants of the female parent selection are pink in color.

Plants of the new *Phalaenopsis* can be compared to plants of the male parent selection. Plants of the new *Phalaenopsis* differ primarily from plants of the male parent selection in the following characteristics:

1. Plants of the new *Phalaenopsis* have white-colored flowers with large red purple-colored lateral spots on the lateral petals whereas plants of the male parent selection are white-colored flowers without spots.
2. The flower labella of plants of the new *Phalaenopsis* are yellow and white in color whereas the flower labella of plants of the male parent selection are orange red in color.

Plants of the new *Phalaenopsis* can be compared to plants of *Phalaenopsis hybrida* 'MI00819', not patented. In side-by-side comparisons, plants of the new *Phalaenopsis* differ primarily from plants of 'MI00819' in the following characteristics:

1. Plants of the new *Phalaenopsis* have shorter inflorescences than plants of 'MI00819'.
2. Plants of the new *Phalaenopsis* have smaller flowers than plants of 'MI00819'.

Plants of the new *Phalaenopsis* can also be compared to plants of *Phalaenopsis hybrida* 'Anastasia 7', not patented. In side-by-side comparisons, plants of the new *Phalaenopsis* differ primarily from plants of 'Anastasia 7' in the following characteristics:

1. Plants of the new *Phalaenopsis* are taller than plants of 'Anastasia 7'.
2. Plants of the new *Phalaenopsis* have white-colored flowers with large red purple-colored lateral spots on the lateral petals whereas plants of 'Anatasia 7' have white-colored flowers with or without spots.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'MI01181' grown in a container.

Figure 2:
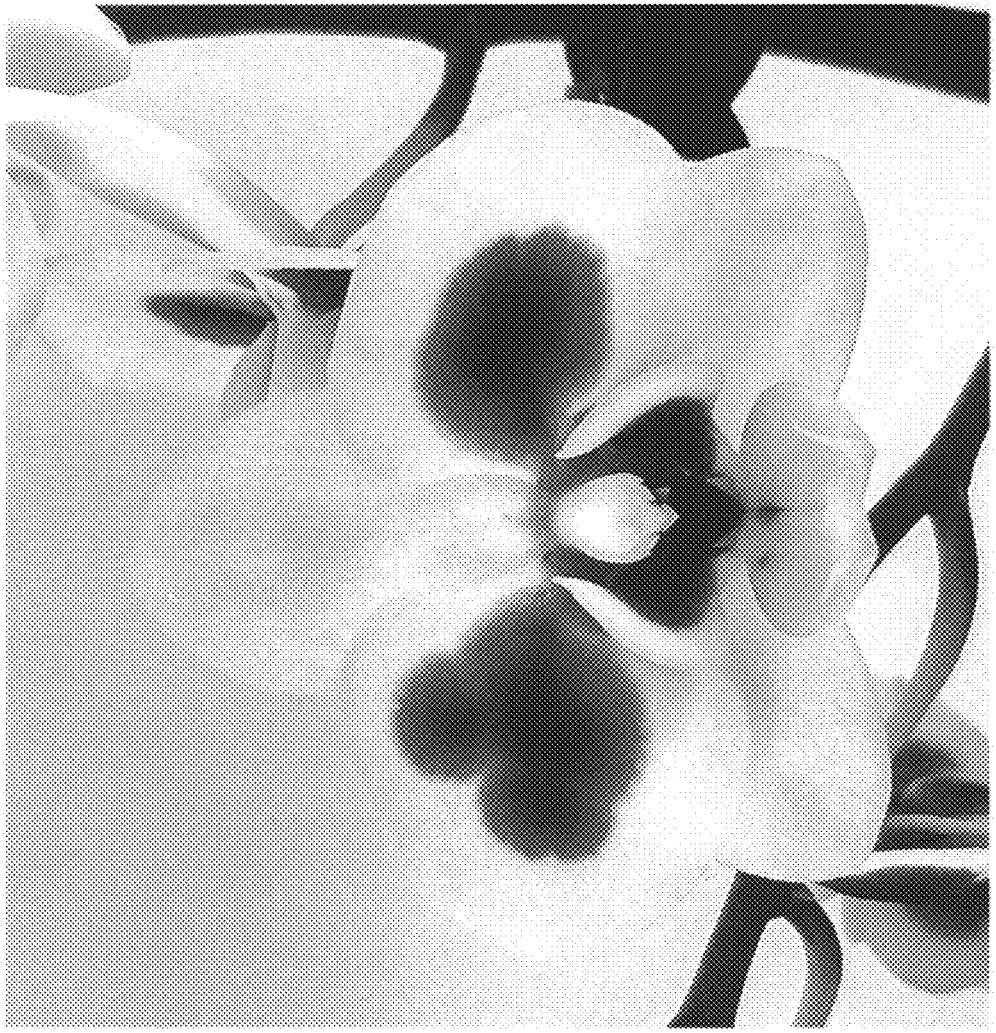

The photograph on the second sheet (FIG. 2) is a close-up view of typical flowers of 'MI01181'.

DETAILED BOTANICAL DESCRIPTION

The aforementioned photographs and following observations and measurements describe plants grown during the late summer in 9-cm containers in a glass-covered greenhouse in Lochristi, Belgium and under cultural practices typically used in commercial *Phalaenopsis* production. During the production of the plants, day and night temperatures ranged from 18° C. to 29° C. and light levels ranged from 150 Watt/$m^2$ to 375 Watt/$m^2$. Plants were 66 weeks old when the photographs and description were taken. In the following description, color references are made to The Royal Horticultural Society Colour Chart, 2015 Edition, except where general terms of ordinary dictionary significance are used.

Botanical classification: *Phalaenopsis hybrida* 'MI01181'.

Parentage:

*Female parent*.—Proprietary selection of *Phalaenopsis hybrida* identified as code number PH01616, not patented.

*Male parent*.—Proprietary selection of *Phalaenopsis hybrida* identified as code number PH01477, not patented.

Propagation:

*Type*.—By in vitro meristem propagation.

*Time to initiate roots, summer*.—About nine to ten weeks at temperatures about 26° C.

*Time to initiate roots, winter*.—About ten to eleven weeks at temperatures about 26° C.

*Time to produce a rooted young plant, summer*.—About 140 to 160 days at temperatures about 26° C.

*Time to produce a rooted young plant, winter*.—About 150 to 180 days at temperatures about 26° C.

*Root description*.—Thick, fleshy; typically grey green in color, towards the apex, close to light green; actual color of the roots is dependent on substrate composition, water quality, fertilizer, substrate temperature and age of roots.

*Rooting habit*.—Small amount of branching; sparse.

Plant description:

*Plant form and growth habit*.—Herbaceous epiphyte; upright plant habit with typically two branched inflorescences per plant, each inflorescence with numerous flowers; monopodial; vigorous growth habit and rapid growth rate.

*Plant height, substrate level to top of foliar plane*.—About 10.5 cm.

*Plant height, substrate level to top of inflorescences*.—About 33.5 cm.

*Plant diameter or spread*.—About 33 cm.

Leaf description:

*Arrangement and quantity*.—Distichous, simple; sessile; about seven leaves per plant.

*Length*.—About 16 cm.

*Width*.—About 5.5 cm.

*Aspect*.—Outwardly arching.

*Shape*.—Elliptic to spatulate.

*Apex*.—Unequal acute.

*Base*.—Sheathing.

*Margin*.—Entire.

*Texture and luster, upper and lower surfaces*.—Slightly furrowed, glabrous; moderately glossy.

*Venation pattern*.—Camptodromous.

*Color*.—Developing leaves, upper surface: Close to NN137A. Developing leaves, lower surface: Close to 146A. Fully expanded leaves, upper surface: Close to 137A; venation, close to 137A. Fully expanded leaves, lower surface: Close to 146A; venation, close to 146A.

Inflorescence description:

*Appearance and flowering habit*.—Showy zygomorphic flowers arranged on axillary branched racemes or panicles; typically two inflorescences per plant; each inflorescence with about 14 open flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about 17 weeks after an inductive cooling period.

*Flower longevity*.—Long flowering period, individual flowers maintain good substance for about 16 weeks on the plant; flowers not persistent; plants of the new *Phalaenopsis* resist bud drop during transport.

*Inflorescence length* (*lowermost flower to inflorescence apex*).—About 16.5 cm.

*Inflorescence width*.—About 7 cm by 16 cm.

*Flower buds*.—Height: About 1.4 cm. Diameter: About 1 cm. Shape: Ovate. Color: Close to 149D tinged with close to 70C.

*Flower diameter*.—Relatively small, about 5 cm.

*Flower depth*.—About 2.9 cm.

*Petals, quantity and arrangement*.—Three, two lateral petals and one center petal transformed into a labellum.

*Lateral petals*.—Length: About 2.2 cm. Width: About 2.5 cm. Shape: Reniform. Apex: Rounded. Margin: Entire. Texture and luster, upper and lower surfaces: Smooth, glabrous, velvety; matte. Color: When opening and fully opened, upper surface: Close to NN155D with spots, close to 79A and N78A. When opening and fully opened, lower surface: Close to NN155D; red purple spots visible from upper surface.

*Labella*.—Appearance: Tri-lobed with two lateral lobes and a central lobe. Length: About 1.4 cm. Width: About 1.3 cm. Shape, lateral lobes: Ovate. Shape, central lobe: Ovate. Apex, lateral lobes: Obtuse. Apex, central lobe: Emarginate with two short, narrow and recurved cirrose tips. Margins, lateral and central lobes: Entire. Texture and luster, upper and lower surfaces: Smooth, glabrous, moderately velvety; matte. Callosities: Located at the base of the labellum and attachment point of the lateral petals; about 6 mm in length, about 4 mm in width and about 2 mm in height. Color: When opening, upper surface: Lateral lobes: Close to NN155D; towards the apex, tinged with close to 10A; towards the base, spot, close to N78A. Central lobe: Close to 155D and 10A; towards the base, some spots, close to N78A. Callosities: Close to 79A. When opening, lower surface: Lateral lobes: Close to NN155D; towards the apex, tinged with close to 10A; towards the base, spot, close to N78A. Central lobe: Close to 155D and 10A. Fully opened, upper surface: Lateral lobes: Close to NN155D; towards the apex, tinged with close to 10A; towards the base, spot, close to N78A. Central lobe: Close to 155D and 10A. Callosities: Close to 79A. When opening, lower surface: Lateral lobes: Close to NN155D; towards the apex, tinged with close to 10A; towards the base, spot, close to N78A. Central lobe: Close to 155D and 10A.

*Sepals*.—Quantity and arrangement: Three, two lower lateral sepals and one upper dorsal sepal. Length, lateral sepal: About 2.5 cm. Width, lateral sepals: About 1.6 cm. Length, dorsal sepal: About 2.6 cm. Width, dorsal sepal: About 1.7 cm. Shape, lateral sepals: Ovate. Shape, dorsal sepal: Elliptic. Apex, lateral sepals: Obtuse. Apex, dorsal sepal: Obtuse to broadly and bluntly acute. Base, lateral and dorsal sepals: Rounded to cuneate. Margin, lateral and dorsal sepals: Entire. Texture and luster, lateral and dorsal sepals, upper and lower surfaces: Smooth, glabrous, velvety; matte. Color, lateral sepals: When opening, upper surface: Close to NN155D slightly overlain with close to 2D; spot, close to N78A. When opening, lower surface: Close to 155D overlain with close to 149B and towards the center, close to 67B. Fully opened, upper surface: Close to NN155D; spot, close to N78A. Fully opened, lower surface: Close to 155D; towards the center, close to 67B. Color, dorsal sepal: When opening and fully opened, upper surface: Close to 155D. When opening and fully opened, lower surface: Close to 155D blushed with close to 67C.

*Peduncles*.—Length: About 36 cm. Diameter: About 4 mm. Strength: Strong, somewhat flexible. Aspect: Upright to about 45° from vertical. Texture and luster: Smooth, glabrous; matte. Color: Close to 138A; fine dots, close to 200B.

*Pedicels*.—Length: About 3.1 cm. Diameter: About 3 mm. Strength: Moderately strong. Aspect: About 85° from peduncle axis. Texture and luster: Smooth, glabrous; matte. Color: Close to 149D; proximally, close to 79A and distally, close to 65D.

*Reproductive organs*.—Androecium: Column length: About 7 mm. Column width: About 4 mm. Column color: Close to 155D. Pollinia quantity: Two. Pollinia diameter (per two pollinia): About 2 mm. Pollinia color: Close to 21A. Gynoecium: Stigma length: About 3 mm. Stigma width: About 2 mm. Stigma shape: Reniform. Stigma color: Close to N155A. Ovary length: About 7 mm. Ovary diameter: About 3 mm. Ovary color: Close to 65D. Seeds and fruits: To date, seed and fruit development have not been observed on plants of the new *Phalaenopsis*.

Pathogen & pest resistance: To date, plants of the new *Phalaenopsis* has been shown to be relatively more tolerant to *Fusarium* spp. than other cultivars of *Phalaenopsis*. To date, plants of the new *Phalaenopsis* have not been shown to be resistant to pests and other pathogens common to *Phalaenopsis* plants.

Temperature tolerance: Plants of the new *Phalaenopsis* have been observed to tolerate high temperatures of about 40° C. and suitable for USDA Hardiness Zone 12.

It is claimed:

1. A new and distinct *Phalaenopsis* plant named 'MI01181' as illustrated and described.

* * * * *